(12) United States Patent
Qi et al.

(10) Patent No.: US 12,159,330 B2
(45) Date of Patent: Dec. 3, 2024

(54) EVENT PROPERTY-DEPENDENT POINT SPREAD FUNCTION MODELING AND IMAGE RECONSTRUCTION FOR PET

(71) Applicant: CANON MEDICAL SYSTEMS CORPORATION, Tochigi (JP)

(72) Inventors: Wenyuan Qi, Vernon Hills, IL (US); Qiang Yi, Vernon Hills, IL (US); Evren Asma, Vernon Hills, IL (US); Li Yang, Vernon Hills, IL (US); Peng Peng, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 478 days.

(21) Appl. No.: 17/674,063

(22) Filed: Feb. 17, 2022

(65) Prior Publication Data

US 2023/0260171 A1     Aug. 17, 2023

(51) Int. Cl.
*G06T 11/00* (2006.01)
*A61B 6/00* (2024.01)
(Continued)

(52) U.S. Cl.
CPC ............ *G06T 11/006* (2013.01); *A61B 6/037* (2013.01); *A61B 6/5282* (2013.01);
(Continued)

(58) Field of Classification Search
CPC ..... A61B 6/037; A61B 6/5282; G01T 1/2985; G06T 11/005; G06T 11/006; G06T 2211/421
See application file for complete search history.

(56) References Cited

U.S. PATENT DOCUMENTS

| 2003/0004405 A1* | 1/2003 | Townsend | A61B 6/463 600/407 |
| 2007/0040122 A1* | 2/2007 | Manjeshwar | G01T 1/2985 250/363.03 |

(Continued)

FOREIGN PATENT DOCUMENTS

| EP | 1 891 462 B1 | 12/2013 |
| EP | 3 576 047 A1 | 12/2019 |

OTHER PUBLICATIONS

Chih Fung Lam, "Correction of Inter-Crystal Scattering Effect in Iterative Image Reconstruction of the jPET-D4", Proceedings Medical Imaging: Physics of Medical Imaging; vol. 6142, 2006, pp. 65-71.

(Continued)

*Primary Examiner* — Blake C Riddick
(74) *Attorney, Agent, or Firm* — Oblon, McClelland, Maier & Neustadt, L.L.P.

(57) ABSTRACT

Upon receiving list-mode data by detecting radiation emitted from a radiation source positioned with a field of view of a medical imaging scanner, each photon included in the list-mode data can be classified according to one or more interaction properties, such as energy or number of crystals interacted with. Grouped pairs of photons can be generated based on the classifying, and a corresponding interaction-property-specific correction kernel (e.g., a corresponding interaction-property-specific point spread function correction kernel) can be selected for each group. Corresponding interaction-property-specific correction kernels can then be utilized to generate higher quality images.

20 Claims, 9 Drawing Sheets

(51) Int. Cl.
*A61B 6/03* (2006.01)
*G01T 1/29* (2006.01)

(52) U.S. Cl.
CPC .......... *G01T 1/2985* (2013.01); *G06T 11/005* (2013.01); *G06T 2211/421* (2013.01)

(56) References Cited

U.S. PATENT DOCUMENTS

| | | | | |
|---|---|---|---|---|
| 2007/0040123 | A1* | 2/2007 | Gagnon | G01T 1/2985 250/363.04 |
| 2010/0303319 | A1* | 12/2010 | Wang | G06T 11/006 382/131 |
| 2012/0049053 | A1* | 3/2012 | Olivier | G06T 1/00 250/252.1 |
| 2012/0089015 | A1 | 4/2012 | Gagnon et al. | |
| 2013/0004050 | A1* | 1/2013 | Wu | A61B 6/483 382/132 |
| 2013/0026370 | A1* | 1/2013 | Qian | G06T 11/005 250/362 |
| 2013/0311142 | A1* | 11/2013 | Wang | G01T 1/2985 702/193 |
| 2014/0212011 | A1* | 7/2014 | Ye | G06T 11/005 382/131 |
| 2015/0199302 | A1* | 7/2015 | Qi | G06T 11/006 703/2 |
| 2015/0363948 | A1* | 12/2015 | Leahy | A61B 6/504 600/425 |
| 2015/0371414 | A1* | 12/2015 | Choi | G01N 23/04 382/131 |
| 2016/0228056 | A1* | 8/2016 | Hooker | A61B 6/508 |
| 2016/0370474 | A1* | 12/2016 | Herraiz | A61B 6/4266 |
| 2017/0046857 | A1* | 2/2017 | Ye | G06T 3/40 |
| 2018/0014806 | A1* | 1/2018 | Lu | A61B 6/032 |
| 2018/0047156 | A1* | 2/2018 | Rudin | G06T 3/40 |
| 2018/0061089 | A1* | 3/2018 | Rong | G21K 1/025 |
| 2019/0287275 | A1* | 9/2019 | Zhu | G06T 7/0012 |
| 2020/0033491 | A1* | 1/2020 | Panin | G01T 7/005 |
| 2020/0170601 | A1* | 6/2020 | Gagnon | A61B 6/4417 |
| 2020/0342638 | A1* | 10/2020 | Liu | G06T 11/005 |
| 2020/0363542 | A1* | 11/2020 | Song | G01T 1/171 |
| 2021/0059629 | A1* | 3/2021 | Hamill | A61B 6/5282 |
| 2021/0183117 | A1* | 6/2021 | Berker | A61B 6/5205 |
| 2021/0290194 | A1* | 9/2021 | Bai | A61N 5/1049 |
| 2022/0079542 | A1* | 3/2022 | Lee | A61B 6/032 |
| 2022/0350037 | A1* | 11/2022 | Panin | G01T 1/2985 |

OTHER PUBLICATIONS

Arman Rahmim, et al., "Resolution modeling in PET imaging: Theory, practice, benefits, and pitfalls," Medical Physics, vol. 40, No. 6, Jun. 2013, pp. 064301-1-064301-15.

Jinyi Qi, et al., "High Resolution 3D Bayesian Image Reconstruction using the microPET Small Animal Scanner," Physics in Medicine & Biology, vol. 43, No. 4, 1998, pp. 1-17.

Li Yang, et al., "Evaluation of Count-Level Adaptive Image Domain PSF for PET Image Reconstruction," IEEE Nuclear Science Symposium and Medical Imaging Conference (NSS/MIC), Oct. 26-Nov. 2, 2019, 2 pages.

A. Rahmim, et al., "Statistical list-mode image reconstruction for the high resolution research tomograph", Institute of Physics Publishing, Physics in Medicine & Biology, vol. 49, 2004, pp. 4239-4258.

* cited by examiner

EVENT PROPERTY-DEPENDENT POINT SPREAD FUNCTION MODELING AND IMAGE RECONSTRUCTION FOR PET

BACKGROUND

Positron emission tomography (PET) imaging begins with the administration (e.g., through ingestion or inhalation) of a radiopharmaceutical agent to a patient. In time, the radiopharmaceutical agent concentrates at specific locations in the human body, thereby exploiting physical and biomolecular properties of the radiopharmaceutical agent to accumulate at regions of interest. The actual spatial distribution, intensity of the point or region of accumulation, and kinetics of the PET imaging process, from administration to capture to elimination, are all elements that may have clinical significance.

During the PET imaging process, the positron emitter attached to the pharmaceutical agent will emit positrons according to the physical properties of the isotope. Emitted positrons collide with an electron of the imaging object, or patient, resulting in an annihilation of the positron and electron and generation of two gamma rays at 511 keV in opposite directions. PET scanners, which include several PET detector rings for detecting the generated gamma rays, typically include a cylindrical bore-type housing supporting the several PET detector rings. Each of the two generated gamma rays interacts with PET detectors of the several PET detector rings and a signal is registered.

PET suffers from several intrinsic spatial resolution degrading factors, including crystal size effects, inter-crystal scattering, crystal penetration, positron range and photon non-collinearity. Most of these factors can be very difficult to measure independently. One technique to account for these factors and to perform resolution recovery is to form an overall point-spread function (PSF). The accuracy of PSF modeling can be critical to image quality.

PSF modeling can be performed in either the sinogram space or image space. In both cases, the kernels are spatially variant because the extent of resolution degradation is highly spatially dependent. In the case of inadequate modeling, resolution recovery can be limited. Over-modeling can potentially cause artifacts in images, such as ring artifacts.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

In one embodiment, the present disclosure is related to a medical imaging scanner, including, but not limited to: processing circuitry configured to receive list-mode data by detecting radiation emitted from a radiation source positioned with a field of view of the medical imaging scanner, each event of a plurality of events within the list-mode data including two photons, classify each photon included in the list-mode data based on at least one interaction property of the photon, generate groups of pairs of photons based on the classification of each photon included in the list-mode data, select, for each group of the grouped pairs of photons, a corresponding interaction-property-specific correction kernel (e.g., a corresponding interaction-property-specific point spread function correction kernel), and apply the corresponding interaction-property-specific correction kernel to data associated with each group of the grouped pairs of photons.

In one embodiment, the present disclosure is related to an image construction method including, but not limited to: receiving list-mode data by detecting radiation emitted from a radiation source positioned with a field of view of an medical imaging scanner, each event of a plurality of events within the list-mode data including two photons; classifying each photon included in the list-mode data based on at least one interaction property of the photon; generating groups of pairs of photons based on the classification of each photon included in the list-mode data; selecting, for each group of the grouped pairs of photons, a corresponding interaction-property-specific correction kernel (e.g., a corresponding interaction-property-specific point spread function correction kernel); and applying the corresponding interaction-property-specific correction kernel to data associated with each group of the grouped pairs of photons.

In one embodiment, the present disclosure is related to a non-transitory computer-readable storage medium storing computer-readable instructions that, when executed by a computer, cause the computer to perform a method for reconstructing a positron emission tomography image including, but not limited to: receiving list-mode data by detecting radiation emitted from a radiation source positioned with a field of view of an medical imaging scanner, each event of a plurality of events within the list-mode data including two photons; classifying each photon included in the list-mode data based on at least one interaction property of the photon; generating groups of pairs of photons based on the classification of each photon included in the list-mode data; selecting, for each group of the grouped pairs of photons, a corresponding interaction-property-specific correction kernel (e.g., a corresponding interaction-property-specific point spread function correction kernel); and applying the corresponding interaction-property-specific correction kernel to data associated with each group of the grouped pairs of photons.

The foregoing paragraphs have been provided by way of general introduction and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Positron emission tomography (PET) is based on the principle of opposed 511 keV photons originating from an annihilation of an emitted positron with a nearby electron. In conventional PET, coincidence electronics are used to determine along which line of response (LOR) an annihilation has occurred. As introduced earlier, conventional approaches, in an effort to localize the annihilation, rely on an equal likelihood that the annihilation occurred at any given point along the LOR. Time-of-flight (TOF) PET goes one step further, determining the likely position of annihilation along the LOR by measuring a difference in arrival times of each photon with a respective PET detector(s).

Among the resolution degrading factors mentioned above, inter-crystal scattering and crystal penetration have a greater influence compared to positron range (for many tracers) and photon non-collinearity. In both of these cases, events with different energy levels or different number of crystal interactions experience different levels of blurring at the sinograms.

Figure 1A:
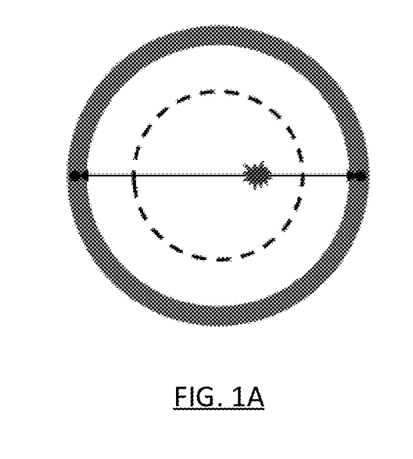
FIGS. 1A-1C illustrate a single-single event, a multi-multi event, and single-multi event, according to an exemplary embodiment of the present disclosure.
Figure 1B:
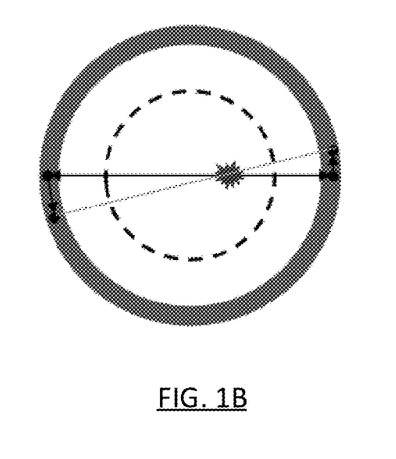
Figure 1C:
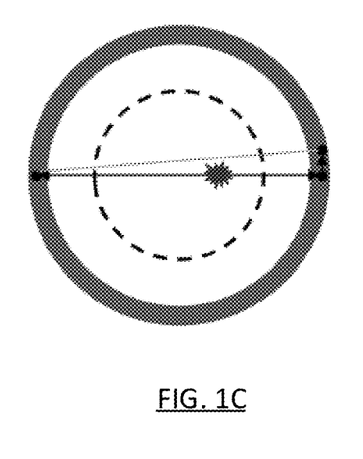

Referring now to the drawings, FIGS. 1A-1C shows how different interactions experience different blurring levels. Each figure shows a pair of singles (i.e. two photons of a coincidence event) that interact with one or more crystals (e.g. due to Compton Scattering). FIG. 1A illustrates a single-single event, where both 511 keV gamma photons interact with one crystal each. FIG. 1B illustrates a multi-multi event, where both 511 keV gamma photons interact with multiple crystals. FIG. 1C shows a single-multi event, where one 511 keV gamma photon interacts with one crystal, and the other 511 keV gamma photon interacts with multiple crystals. In the latter two cases, the multi-crystal interactions (e.g. via Compton Scattering) generate an inaccurate line of response, which can lead to lower quality images. In order to further improve PSF modeling accuracy, event-property-dependent PSF modeling can be utilized. Both sinogram and image domain implementations will be discussed herein.

Figure 2:
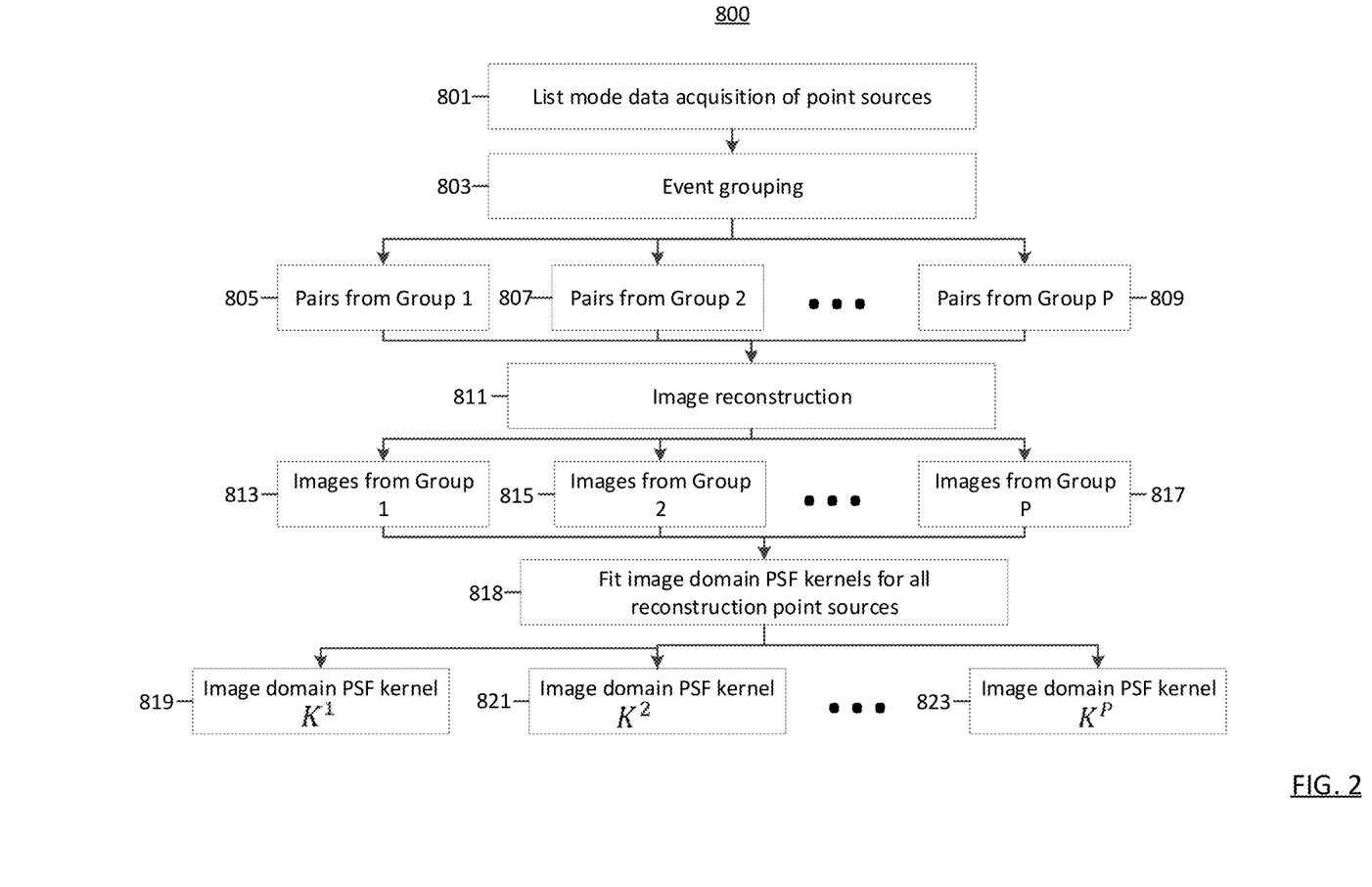
FIG. 2 illustrates a method for event-property-dependent image domain PSF modeling, according to an exemplary embodiment of the present disclosure.

FIG. 2 shows a method 800 for event-property-dependent PSF modelling in the image domain. In step 801, acquire a list mode data acquisition of point sources. In one embodiment, this looks like scanning an object (e.g. patient) in a medical imaging scanner (e.g. PET scanner) to collect the list mode data.

In step 803, perform event grouping using the list mode data. In this exemplary embodiment, the event grouping generates P groups of pairs of photons: pairs from group 1 805, pairs from group 2 807, . . . , and pairs from group P 809, where P is greater than or equal to three. Of course, any number of groups can be made in other instances. Event grouping groups the list mode data acquired in step 801 into one or more groups based on at least one interaction property (e.g. crystal size, inter-crystal scattering, crystal penetration, position range, photon non-collinearity). Additional details on step 803 are discussed later with reference to FIG. 4 and FIG. 5.

Step 811 is to perform image reconstruction on pairs from group 1 805, pairs from group 2 807, through pairs from group P 809 to generate images from group 1 813, images from group 2 815, through images from group P 817, respectively. Any image reconstruction technique can be used, such as filtered back projection.

Step 818 is to fit respective image domain PSF kernels for all reconstruction point sources from images from group 813, images from group 2 815, through images from group P 817, to generate image domain PSF kernel $K^1$ 819, image domain PSF kernel $K^2$ 821, through image domain PSF kernel $K^P$ 823, respectively.

After obtaining the PSF kernels, they can be applied to the data associated with each group of the grouped pairs of photon. For instance, image domain PSF kernel $K^1$ 819 can be applied to images from group 1 813, image domain PSF kernel $K^2$ 821 can be applied to images from group 2 813, and image domain PSF kernel $K^P$ 223 can be applied to images from group P 817.

In List-mode reconstruction, the list-mode expectation maximization (LMEM) reconstruction algorithm can be derived from an expression for the likelihood function for statistically independent, Poisson-distributed sinogram data, where the sum over sinogram bins is converted to a summation over events. One such configuration is described in *Statistical list-mode image reconstruction for the high resolution research tomograph*, by Rahmim et al. 2004 (0031-9155/04/184239), incorporated herein by reference. The estimated image f̄ is updated according to:

$$\bar{f}_j^{k+1} = \frac{\bar{f}_j^k}{s_j} \sum_b^B H_{i_b j} \frac{1}{\sum_{n=0}^{N-1} H_{i_b n} \bar{f}_n^k} \quad (1)$$

where H is the system matrix, $s_j = \Sigma_i H_{ij}$. N is the total number of voxels in the image. B is the total number of events, $i_b$ denotes the ith Line of Response (LOR) at which the bth event is detected.

For regular image domain PSF reconstruction, the estimated image will be convoluted by PSF kernel as shown in equation (2), and then forward projected. The backward projection will be deconvoluted by inverse of the PSF kernel.

$$\bar{f}_j^{k+1} = \frac{\bar{f}_j^k}{\sum_{l=0}^{N-1} K_{jl} s_l} \sum_{l=0}^{N-1} K_{lj} \sum_{i_b}^{B} H_{i_b j} \frac{1}{\sum_{n=0}^{N-1} H_{i_b n} \sum_{l'=0}^{N-1} K_{nl'} \bar{f}_{l'}^k} \quad (2)$$

where $K_{lj}$ denotes the blurring from voxel j to voxel l.

For event-property-dependent PSF reconstruction, the update can be performed by dividing the list-mode events into several groups, with the PSF kernels potentially different for each group. During the reconstruction, the PSF model will be selected for each group, and the final reconstruction will be based on all the groups as shown by equation (3).

$$\bar{f}_j^{k+1} = \bar{f}_j^k \sum_p^P \frac{1}{\sum_{l=0}^{N-1} K_{jl}^p s_l} \sum_{l=0}^{N-1} K_{lj}^p \sum_{i_b \in G_p} H_{i_b j} \frac{1}{\sum_{n=0}^{N-1} H_{i_b n} \sum_{l'=0}^{N-1} K_{nl'}^p \bar{f}_{l'}^k} \quad (3)$$

where $K_{lj}^p$ is the resolution recovery factor from $G_p$.

Figure 3:
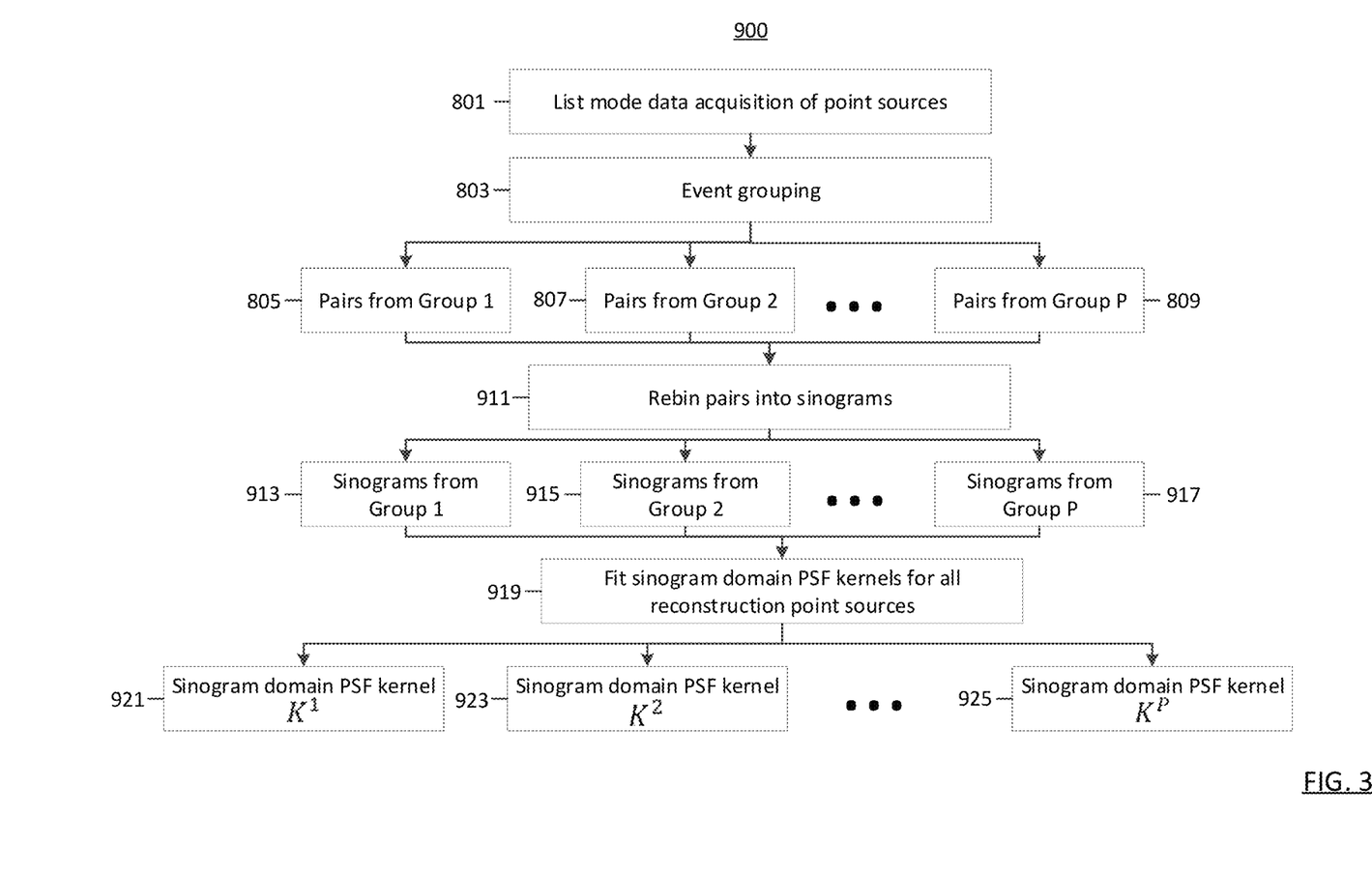
FIG. 3 illustrates a method for event-property-dependent sinogram domain PSF modeling, according to an exemplary embodiment of the present disclosure.

FIG. 3 shows a method 900 for event-property-dependent PSF modeling in the sinogram domain. Method 900 is similar to method 800 in that steps 801 and 803 from method 800 are repeated to generate pairs from group 1 805, pairs from group 2 807, . . . , and pairs from group P 809. Then in step 911, instead of performing image reconstruction, each group of pairs are rebinned into sinograms to create sinograms from group 1 913, sinograms from group 2 915, . . . , and sinograms from group P 917. In step 919, each of sinograms from group 1 913, sinograms from group 2 915, . . . , and sinograms from group P 917 are used in fitting to generate sinogram domain PSF kernel $K^1$ 921, sinogram domain PSF kernel $K^2$ 923, . . . , and sinogram domain PSF kernel $K^P$ 925, respectively. Each of these kernels can be applied to their respective sinogram groups.

For regular sinogram domain PSF list-mode reconstruction, the update can be determined with equation (4) where the sinogram is convoluted with a PSF kernel. There will be deconvolution with the inverse of PSF kernels before the backward projection.

$$\bar{f}_j^{k+1} = \frac{\bar{f}_j^k}{s_j} \sum_{i_b}^B \sum_l H_{lj} K_{i_b l} \frac{1}{\sum_{l'=0}^{M-1} K_{i_b l'} \sum_{n=0}^{N-1} H_{l'n} \bar{f}_n^k} \quad (4)$$

where $K_{lj}$ is the resolution recovery factor from element j to element l in sinogram. M is the total number of element in sinogram.

For multi-resolution PSF reconstruction, the list mode event can be divided into several groups, with each group uses the same PSF kernel modeling for sinogram domain PSF modeling with the final reconstruction based on the updates of all the groups according to an equation similar to that of equation (5).

$$\bar{f}_j^{k+1} = \frac{\bar{f}_j^k}{s_j} \sum_p^P \sum_{i_b \in G_p} \sum_l H_{lj} K_{i_b l}^p \frac{1}{\sum_{l'=0}^{M-1} K_{i_b l'}^p \sum_{n=0}^{N-1} H_{l'n} \bar{f}_n^k} \quad (5)$$

where $K_{lj}^p$ is the resolution recovery factor from $G_p$.

Figure 4:
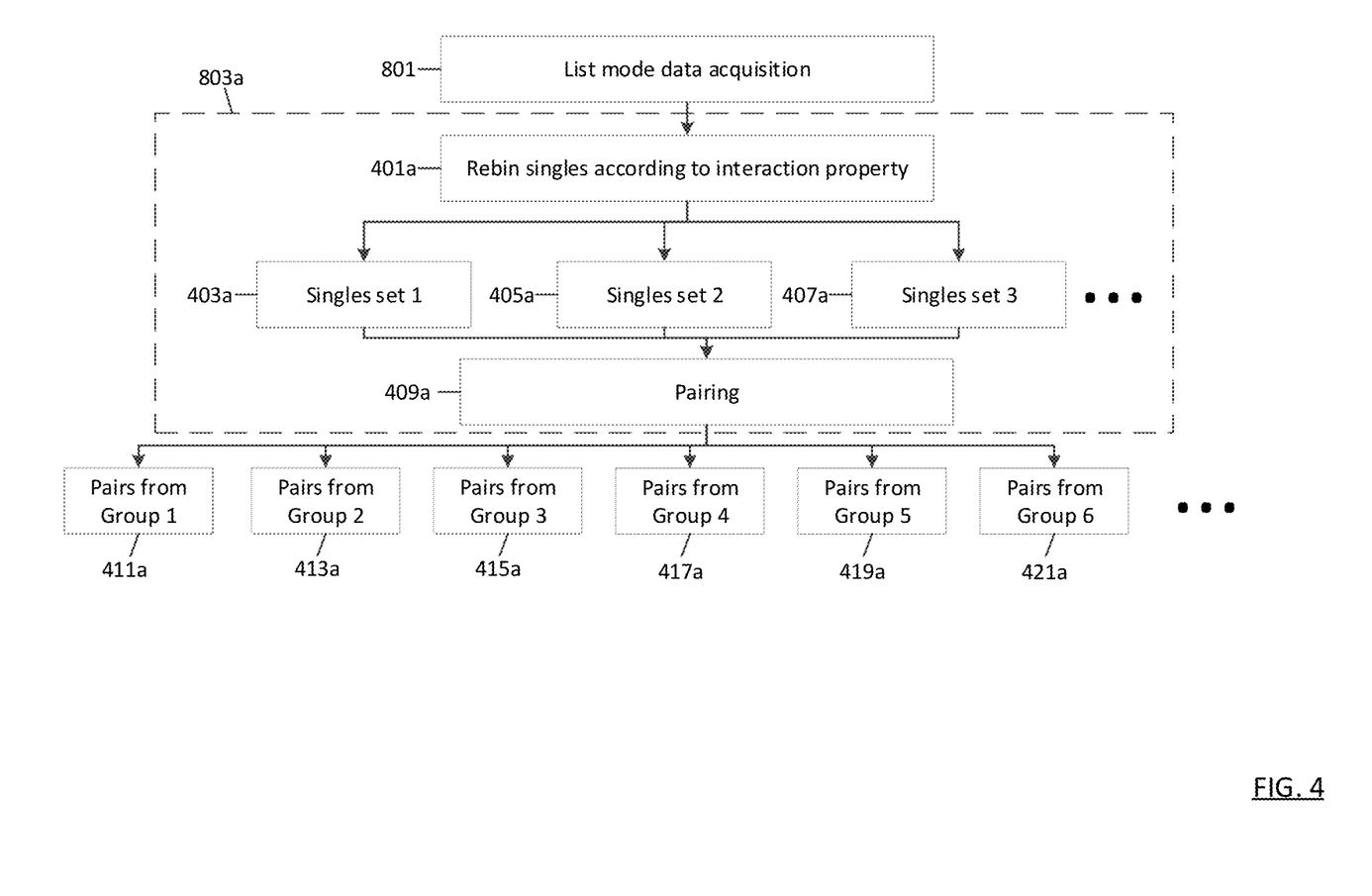
FIG. 4 illustrates a method for event grouping, according to an exemplary embodiment of the present disclosure.

Moving to FIG. 4, FIG. 4 shows the steps of a method 803*a* for performing the event grouping in step 803. The input of method 803*a* is the list mode data acquisition of point sources from step 801, and the output of method 803*a* is one or more groups of pairs.

Step 401*a* is to rebin singles in the list mode data according to one or more interaction properties to generate singles set 1 403*a*, singles set 2 407*a*, singles set 3 407*a*, et cetera. Any number of singles can be created.

In one embodiment, an interaction property is the number of crystals a photon has interacted with. The amount of single sets can correspond to the range of number of crystals that photons have interacted with. For example, if photons have interacted with anywhere from one to three crystals, three single sets can be generated.

In one embodiment, an interaction property is the event energy of the photons in the list mode data. Any number of single sets can be created to contain photons having an event energy within a predetermined range of energies for each set. For example, a first single set can contain photons with event energy greater than 500 keV, a second set can contain photons with event energy between 399-500 keV, a third set can contain photons with event energy between 300-400 keV, and a fourth set can contain photons with event energy beneath 300 keV.

Step 409 is to perform pairing of the singles to form coincidence events. Groups are formed for each possible pairing of singles. For instance, as shown in FIG. 4, pairs from group 1 411*a*, pairs from group 2 413*a*, pairs from group 3 415*a*, pairs from group 4 417*a*, pairs from group 5 419*a*, and pairs from group 6 421*a* are created based on singles set 1 403*a*, singles set 2 405*a*, and singles set 3 407*a*. That is, six groups are formed via pairing in step 409*a* based on the possible pairing combinations of the three sets of singles: (1) a single from set 1 403*a* paired with a single from set 1 403*a*; (2) a single from set 1 403*a* paired with a single from set 2 405*a*; (3) a single from set 1 403*a* paired with a single from set 3 407*a*; (4) a single from set 2 405*a* paired with a single from set 2 405*a*; (5) a single from set 2 405*a* paired with a single from set 3 407*a*; and (6) a single from set 3 407*a* paired with a single from set 3 407*a*. Each of these groups can then be utilized in generating respective PSF kernels.

Figure 5:
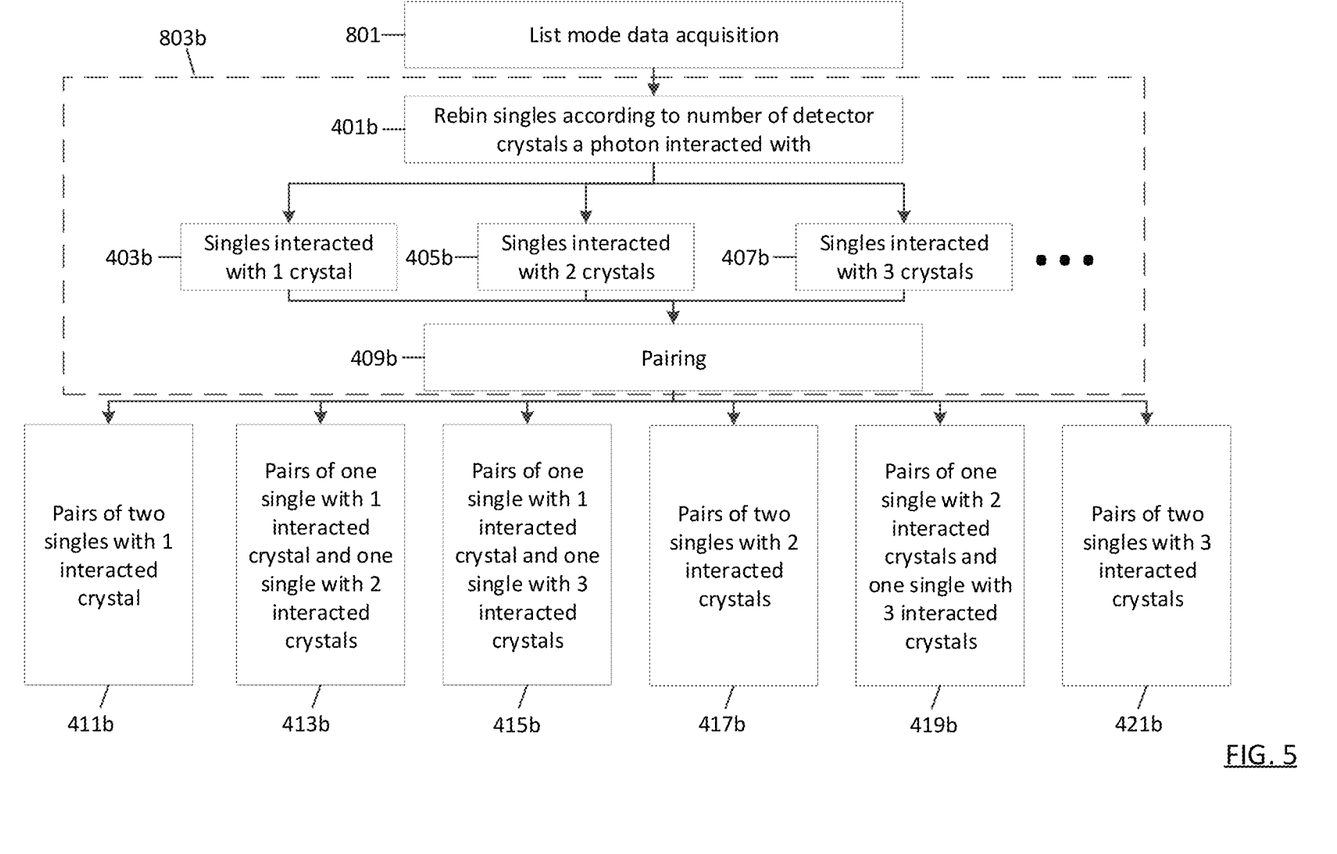
FIG. 5 illustrates a method for event grouping based on the number of detector crystals a photon interacted with, according to an exemplary embodiment of the present disclosure.

FIG. 5 outlines a flowchart for a method 803*b* to perform event grouping based on the number of detector crystals a photon interacts with, according to one exemplary embodiment. In step 401*b*, each photon included in the list-mode data acquired in step 801 can be classified according to the number of detector crystals each photon interacted with. In this example, the number of detector crystals includes singles that interacted with 1 crystal 405*b*, singles that interacted with 2 crystals 405*b*, and singles that interacted with 3 crystals 407*b*. Pairing in step 409*b* pairs singles to generate coincidence event pairs in six different groups: (1) pairs of two singles with 1 interacted crystals 411*b*; (2) pairs of one single with 1 interacted crystal and one single with 2 interacted crystals 413*b*; (3) pairs of one single with 1 interacted crystal and one single with 3 interacted crystals 415*b*; (4) pairs of two singles with 2 interacted crystals 417*b*; (5) pairs of one single with 2 interacted crystals and one single with 3 interacted crystals 419*b*; and (6) pairs of two singles with 3 interacted crystals 421*b*. Each of these six groups can be utilized in generated respective PSF kernels.

Figure 6:
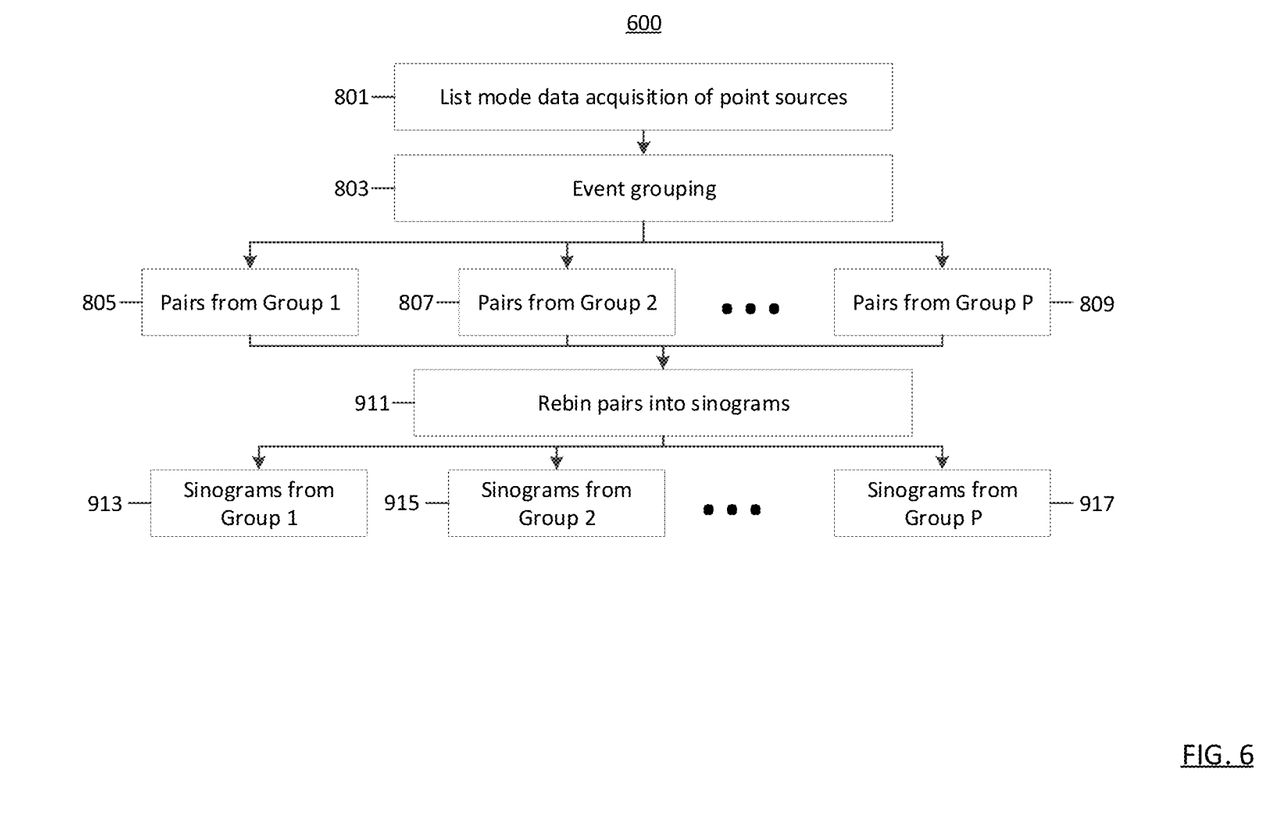
FIG. 6 illustrates a method for multi-resolution PSF reconstruction, according to an exemplary embodiment of the present disclosure.

FIG. 6 shows a flowchart for a method 600 related to multi-resolution PSF sinogram reconstruction. Method 600 includes steps 801, 803, and 911, as discussed previously with respect to method 800/900. The update in the image domain PSF sinogram reconstruction:

$$\bar{f}_j^{k+1} = \bar{f}_j^k \sum_p^P \frac{1}{\sum_{l=0}^{N-1} K_{lj}^p s_l} \sum_{l=0}^{N-1} K_{lj}^p \sum_i H_{il} \frac{g_i^p}{\sum_{n=0}^{N-1} H_{in} \sum_{i'=0}^{N-1} K_{ni'}^p \bar{f}_{i'}^k} \quad (6)$$

The update in sinogram domain PSF sinogram reconstruction is:

$$\bar{f}_j^{k+1} = \frac{\bar{f}_j^k}{s_j} \sum_p^P \sum_i H_{ij} K_{ii}^p \frac{g_i^p}{\sum_{i'=0}^{M-1} K_{ii'}^p \sum_{n=0}^{N-1} H_{i'n} \bar{f}_n^k} \quad (7)$$

where $g_i^p$ is the ith element in sinogram from group P.

Similar to list-mode multi resolution PSF, the total sinogram of the data as determined in equation (7) is divided into several groups of sinogram, and each group potentially using different PSF kernels, and the final reconstruction is based all the groups of sinograms.

In image mode reconstruction, ordered subsets may be used to reduce the reconstruction time. While the convergence rate is image dependent, conventional maximum likelihood expectation maximization (ML-EM) reconstruction requires approximately 20-50 iterations. One such technique is described in *Ordered Subsets Expectation Maximization* (*OSEM*) by [H. M. Hudson and R. S. Larkin, IEEE Trans Med Imaging, Vol. 13], 1994 (the contents of which are incorporated herein by reference) in order to reduce the number of iterations. OSEM uses subsets of the entire data set for each image update in the form of equation (8) where the backprojection steps sum over only the projections in subset $S_b$ of a total of B subsets. Therefore the image is updated during each subiteration and one complete iteration will have B image updates. This image mode reconstruction or similar OSEM method may be applied to the group data associated with each group of the grouped pairs of photons.

$$f_j^{(n+1)} = \frac{\hat{f}_j^{(n)}}{\sum_{i' \in S_b} H_{i'j}} \sum_{i \in S_b} H_{ij} \frac{p_i}{\sum_k H_{ik} \hat{f}_k^{(n)}} \quad (8)$$

Figure 7:
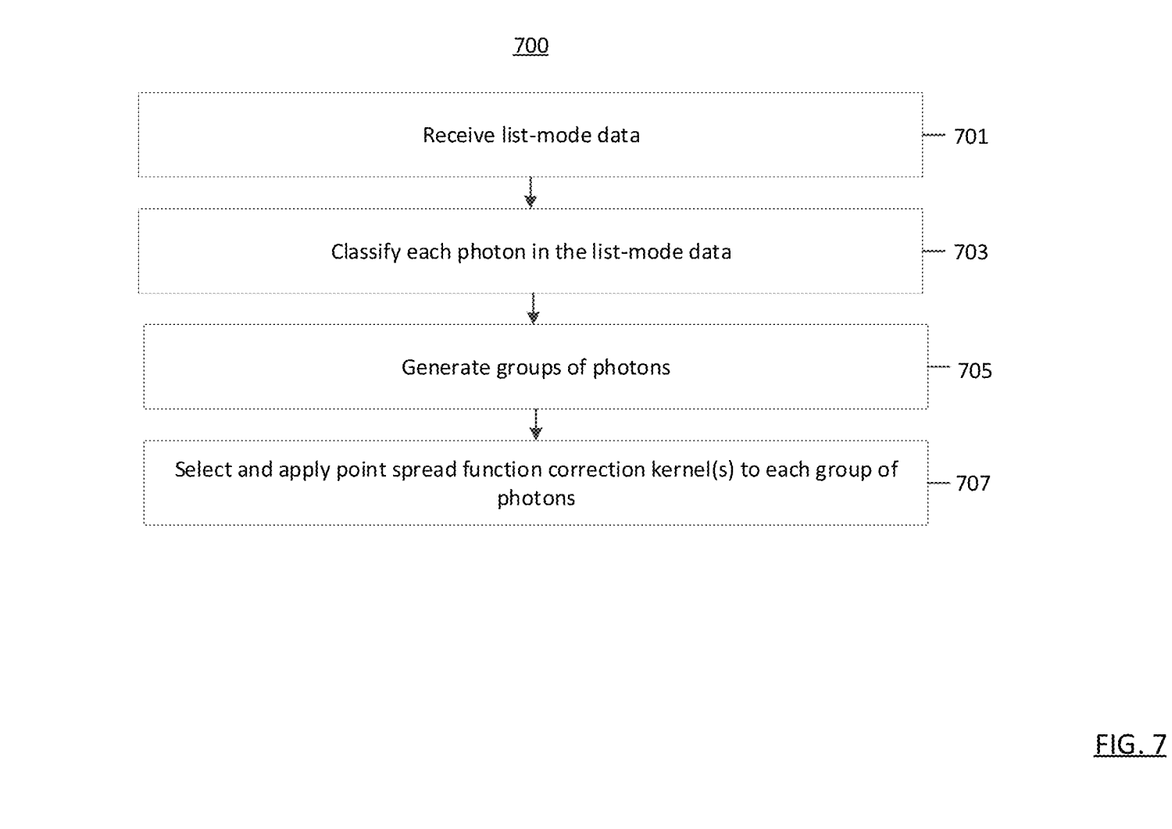
FIG. 7 illustrates a method for event-property-dependent PSF modeling, according to an exemplary embodiment of the present disclosure.

FIG. 7 shows a flowchart for a method 700, according to one embodiment of the present disclosure. Step 701 is to receive list-mode data. This can look like acquiring imaging data from a scan of an object, such as a PET scan of a patient. The list-mode data can include the energy and location of each photon event.

Step 703 is to classify each photon in the list-mode data. The classifying can be done based on one or more interaction properties of the photons. Examples of interaction properties include the number of detector crystals a photon interacts with, and an energy with which the photon interacts with detector crystals.

Step 705 is to generate one or more groups of photons based on the classification of each photon included in the list-mode data. The various possible pairing combinations of the photons based on their one or more interaction properties can each generate a group of photons. Each of these groups can then be rebinned into sinograms if the PSF modeling is done in the sinogram domain, or image reconstructed if the PSF modeling is done in the image domain, as previously discussed.

Step 707 is to select and apply one or more point spread function correction kernels to each of the one or more groups of photons. In one embodiment, if the PSF modeling is done in the sinogram domain, this can be done using Equations (5) or (6). In one embodiment, if the PSF modeling is done in the image domain, this can be done using Equation (3) or (6).

Upon completion of method 700, an image can be generated. In one embodiment, this can include compiling corrected groups of data and performing image reconstruction. Further, the image can be displayed on a display. Although steps 701, 703, 705, and 707 are performed serially, steps within each step can be performed in series and/or in parallel. For example, in step 705, each group of photons can be created in series and/or in parallel. As another example, each of the PSF kernels can be applied in series and/or in parallel.

Figure 8:
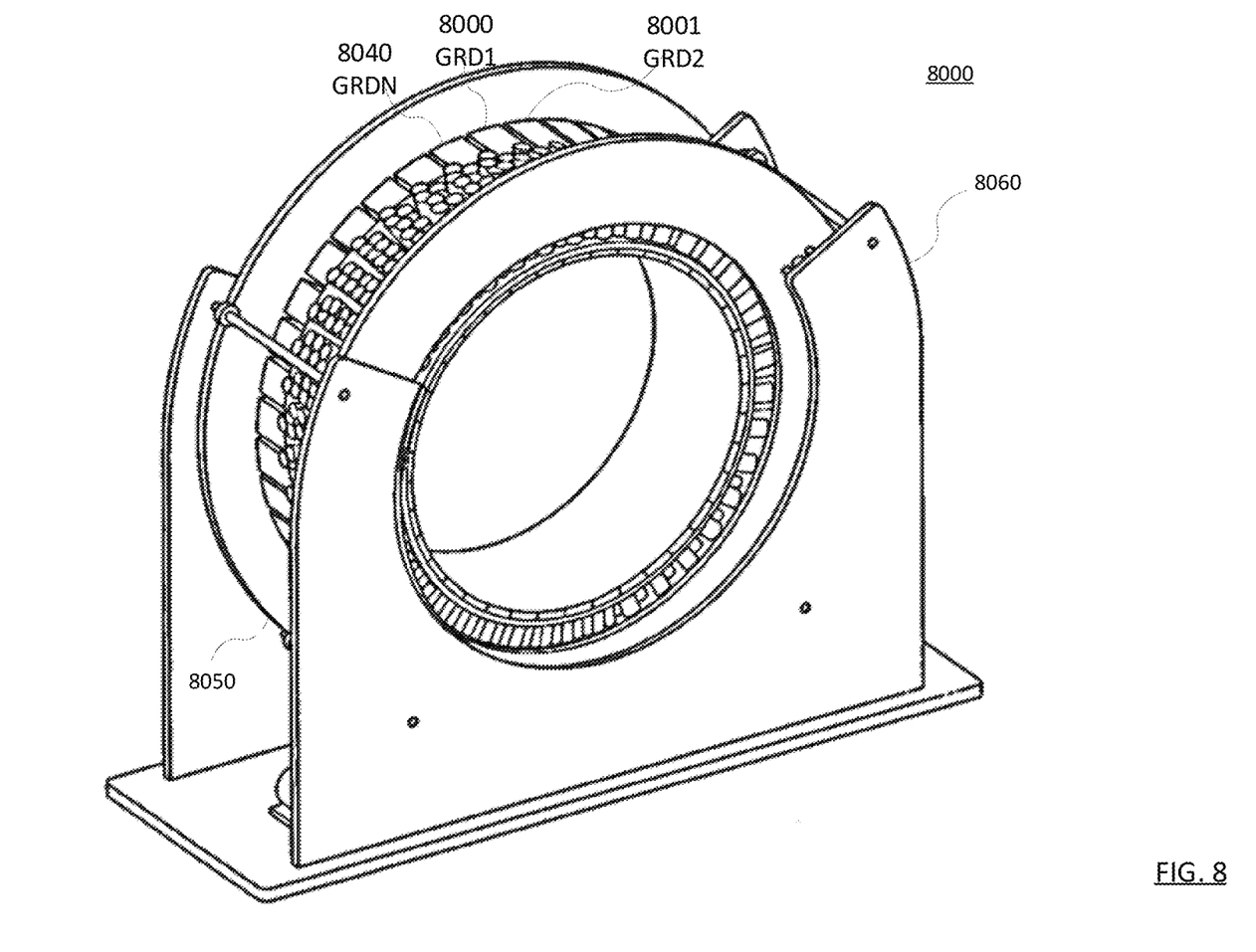
FIG. 8 is an illustration of a perspective view of a PET scanner, according to an exemplary embodiment of the present disclosure.
Figure 9:
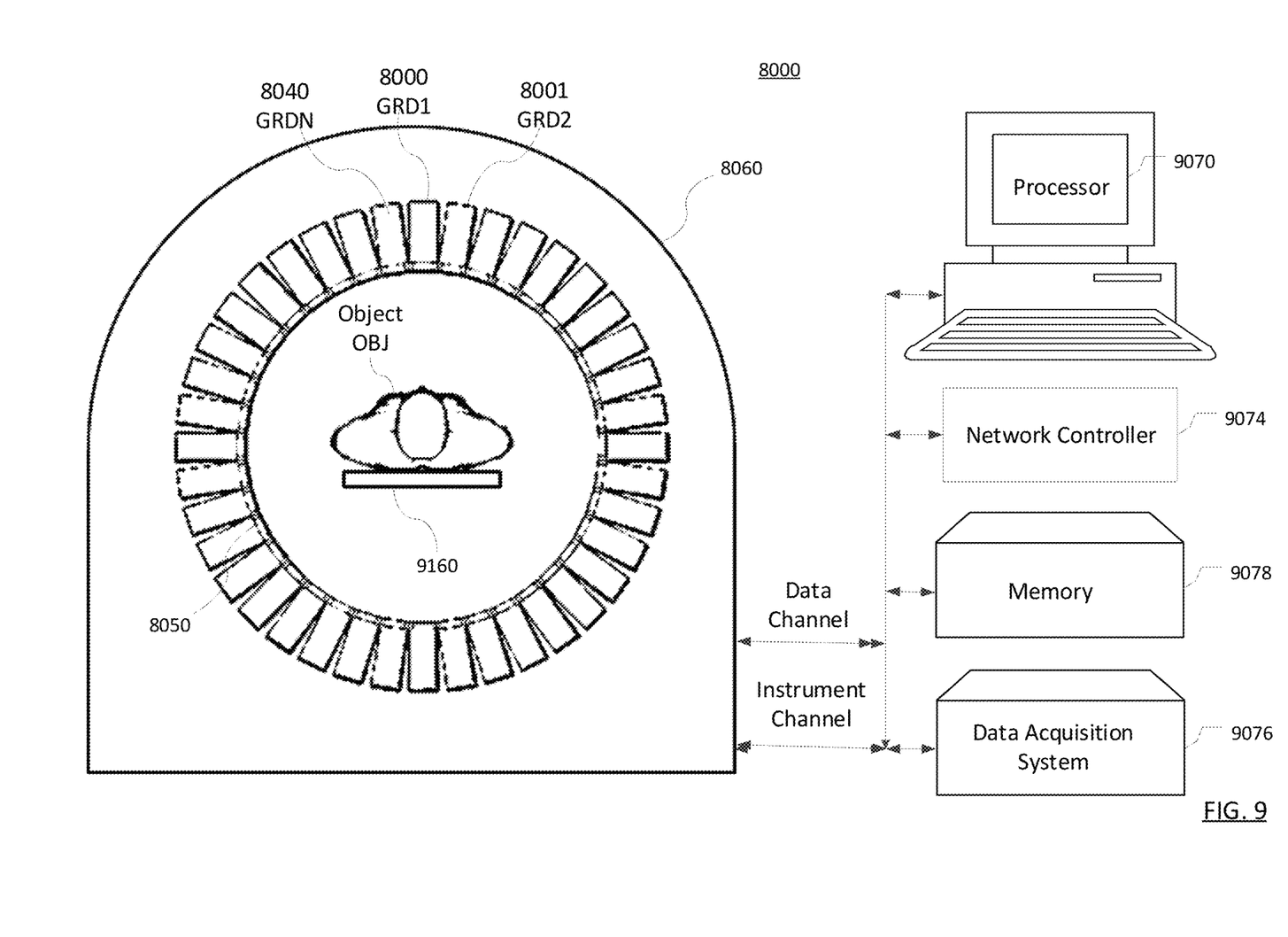
FIG. 9 is a schematic of a PET scanner and associated hardware, according to an exemplary embodiment of the present disclosure.

In an embodiment, it can be appreciated that the methods of the present disclosure may be implemented within a PET scanner, as shown in FIG. 8 and FIG. 9. Therefore, FIG. 8 and FIG. 9 show a PET scanner 8000 including a number of gamma-ray detectors (GRDs) 8001, 8002 . . . 8040 (e.g., GRD1, GRD2, through GRDN) that are each configured as rectangular detector modules. The PET scanner 8000 may be an adaptive axial Field of View (aaFOV) PET scanner, as introduced above. According to one implementation, each PET detector ring, which forms a cylindrical bore 8050 about a gantry 8060 includes, for example, 40 GRDs. In another implementation, there are 48 or more GRDs, the higher number of GRDs being used to create a larger bore size for the PET scanner 8000. As in the present disclosure, each PET detector ring may be independently translatable about an axial length of the aaFOV PET scanner. The translation of each PET detector ring may be accomplished by manual manipulation and/or motorized manipulation. The GRDs include scintillator crystal arrays for converting the gamma rays into scintillation photons (e.g., at optical, infrared, and ultraviolet wavelengths), which are detected by photodetectors. Each GRD can include a two-dimensional array of individual detector crystals, which absorb gamma radiation and emit scintillation photons. The scintillation photons can be detected by a two-dimensional array of photomultiplier tubes (PMTs) that are also arranged in the GRD. A light guide can be disposed between the array of detector crystals and the PMTs. Further, each GRD can include a number of PMTs of various sizes, each of which is arranged to receive scintillation photons from a plurality of detector crystals. Each PMT can produce an analog signal that indicates when scintillation events occur, and an energy of the gamma ray producing the detection event. Moreover, the photons emitted from one detector crystal can be detected by more than one PMT, and, based on the analog signal produced at each PMT, the detector crystal corresponding to the detection event can be determined using Anger logic and crystal decoding, for example. However, Anger arithmetic is not necessarily required when there is a one-to-one correspondence between the crystals and the photodetectors.

FIG. 9 shows a schematic view of a PET scanner system having GRDs 8001, 8002 . . . 8040 arranged to detect gamma-rays emitted from an object OBJ. The GRDs can measure the timing, position, and energy corresponding to each gamma-ray detection. In one implementation, the gamma-ray detectors are arranged in a PET detector ring, as shown in FIG. 8 and FIG. 9, and as described herein. It can be appreciated that the single PET detector ring of FIG. 9 can be extrapolated to include any number of PET detector rings along an axial length of the PET scanner. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 9 shows an example of the arrangement of the PET scanner 8000, in which the object OBJ to be imaged rests on a table 9160 and the GRD modules GRD1 8001 through GRDN 8040 are arranged circumferentially around the object OBJ and the table 9160. The GRDs may comprise a PET detector ring and may fixedly-connected to a cylindrical bore 8050 that is fixedly-connected to a gantry 8060. The gantry 8060 houses many parts of the PET scanner. The gantry 8060 of the PET scanner also includes an open aperture, defined by the cylindrical bore 8050, through which the object OBJ and the table 9160 can pass, and gamma-rays emitted in opposite directions from the object OBJ due to an annihilation event can be detected by the GRDs and timing and energy information can be used to determine coincidences for gamma-ray pairs.

In FIG. 9, circuitry and hardware is also shown for acquiring, storing, processing, and distributing gamma-ray detection data. The circuitry and hardware include a processor 9070, a network controller 9074 303, a memory 9078, and a data acquisition system (DAS) 9076. The PET imager also includes a data channel that routes detection measurement results from the GRDs to the DAS 9076, the processor 9070, the memory 9078, and the network controller 9074. The DAS 9076 can control the acquisition, digitization, and routing of the detection data from the detectors. In one implementation, the DAS 9076 controls the movement of the table 9160. The processor 9070 performs functions including adjusting PET detector rings, pre-reconstruction processing of the detection data, image reconstruction, and post-reconstruction processing of the image data.

According to an embodiment, the processor 9070 of the PET scanner 8000 of FIG. 8 and FIG. 9 can be configured to perform any of the methods described herein, as well as variations thereof. The processor 9070 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 9078 can be a hard disk drive, CD-ROM drive, DVD drive, FLASH drive, RAM, ROM or any other electronic storage known in the art. The memory 9078 may be non-volatile, such as ROM, EPROM, EEPROM or FLASH memory. The memory 9078 can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 9070 can execute a computer program including a set of computer-readable instructions that perform the methods described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a XENON® processor from Intel of America or an OPTERON® processor from AMD of America and an operating system, such as Microsoft VISTA®, UNIX, Solaris®, LINUX, Apple MAC-OS® and other operating systems known to those skilled in the art. Further, CPU can be implemented as multiple processors locally or in a distributed cloud configuration cooperatively working in parallel to perform the instructions.

In one implementation, the PET scanner may include a display for displaying a reconstructed image and the like. The display can be an LCD display, CRT display, plasma display, OLED, LED or any other display known in the art.

The network controller 9074, such as an Intel Ethernet PRO network interface card from Intel Corporation of America, can interface between the various parts of the PET imager. Additionally, the network controller 9074 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including GPRS, EDGE, 3G, 4G and 5G wireless cellular systems. The wireless network can also be Wi-Fi, Bluetooth, or any other wireless form of communication that is known.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) A medical imaging scanner, including, but not limited to: processing circuitry configured to: receive list-mode data, generated by detecting radiation emitted from a radiation source positioned with a field of view of the medical imaging scanner, each event of a plurality of events within the list-mode data including two photons, classify each photon included in the list-mode data based on at least one interaction property of the photon, generate grouped pairs of photons based on the classification of each photon included in the list-mode data based on the at least one interaction property of the photon, select, for each group of the grouped pairs of photons, a corresponding interaction-property-specific point spread function correction kernel, and apply the corresponding interaction-property-specific point spread function correction kernel to data associated with each group of the grouped pairs of photons.

(2) The medical imaging scanner of (1) wherein the data associated with each group of the grouped pairs of photons is image data.

(3) The medical imaging scanner of any of (1) to (2), wherein the data associated with each group of the grouped pairs of photons is sinogram data.

(4) The medical imaging scanner of any of (1) to (3), wherein the at least one interaction property includes a number of detector crystals a photon interacts with.

(5) The medical imaging scanner of any of (1) to (4), wherein the at least one interaction property includes an energy with which each photon interacts with detector crystals.

(6) The medical imaging scanner of any of (1) to (5) wherein the processing circuitry is further configured to display an image based on the data associated with each group of the grouped pairs of photons after applying the corresponding interaction-property-specific correction kernel.

(7) The medical imaging scanner of any of (1) to (6), wherein the processing circuitry is further configured to display an image based on the data associated with each group of the group pairs of photons wherein ordered subset expectation maximization uses interaction-property-specific correction kernel on subsets of the entire data set for each image update.

(8) The medical imaging scanner of any of (1) to (7), wherein the processing circuitry configured to select, for each group of the grouped pairs of photons, a corresponding interaction-property-specific correction kernel, and apply the corresponding interaction-property-specific correction kernel to data associated with each group of the grouped pairs of photons includes, but is not limited to, processing circuitry configured to select, for each group of the grouped pairs of photons, a corresponding interaction-property-specific point spread function correction kernel, and apply the corresponding interaction-property-specific point spread function correction kernel to data associated with each group of the grouped pairs of photons.

(9) An image construction method including, but not limited to: receiving list-mode data generated by detecting radiation emitted from a radiation source positioned with a field of view of an medical imaging scanner, each event of a plurality of events within the list-mode data including two photons; classifying each photon included in the list-mode data based on at least one interaction property of the photon; generating grouped pairs of photons based on a result of the classifying of each photon included in the list-mode data based on at least one interaction property of the photon; selecting, for each group of the grouped pairs of photons, a corresponding interaction-property-specific correction kernel; and applying the corresponding correction kernel to data associated with each group of the grouped pairs of photons.

(10) The method of (9), wherein the data associated with each group of the grouped pairs of photons is image data.

(11) The method of any of (9) to (10), wherein the data associated with each group of the grouped pairs of photons is sinogram data.

(12) The method of any of (9) to (11), wherein the at least one interaction property includes a number of detector crystals a photon interacts with.

(13) The method of any of (9) to (12), wherein the at least one interaction property includes an energy with which the photon interacts with detector crystals.

(14) The method of any of (9) to (13), further comprising displaying an image based on the data associated with each group of the grouped pairs of photons after applying the corresponding interaction-property-specific correction kernel.

(15) The method of any of (9) to (14), wherein the corresponding interaction-property-specific correction kernel uses ordered subset expectation maximization on subsets of the entire data set for each image update.

(16) The method of any of (9) to (15), wherein selecting, for each group of the grouped pairs of photons, a corresponding interaction-property-specific correction kernel, and apply the corresponding interaction-property-specific correction kernel to data associated with each group of the grouped pairs of photons includes, but is not limited to, selecting, for each group of the grouped pairs of photons, a corresponding interaction-property-specific point spread function correction kernel, and applying the corresponding interaction-property-specific point spread function correction kernel to data associated with each group of the grouped pairs of photons.

(17) A non-transitory computer-readable storage medium storing computer-readable instructions that, when executed by a computer, cause the computer to perform a method for reconstructing a positron emission tomography image including, but not limited to: receiving list-mode data generated by detecting radiation emitted from a radiation source positioned with a field of view of an medical imaging scanner, each event of a plurality of events within the list-mode data including two photons; classifying each photon included in the list-mode data based on at least one interaction property of the photon; generating grouped pairs of photons based on a result of the classifying of each photon included in the list-mode data based on at least one interaction property of the photon; selecting, for each group of the grouped pairs of photons, a corresponding interaction-property-specific correction kernel; and applying the correction kernel to data associated with each group of the grouped pairs of photons.

(18) The non-transitory computer-readable storage medium according to (17), wherein the data associated with each group of the grouped pairs of photons is image data.

(19) The non-transitory computer-readable storage medium according to any of (17) to (18), wherein the data associated with each group of the grouped pairs of photons is sinogram data.

(20) The non-transitory computer-readable storage medium according to any of (17) to (19), wherein the at least one interaction property includes a number of detector crystals a photon interacts with.

(21) The non-transitory computer-readable storage medium according to any of (17) to (20), wherein the at least one interaction property includes an energy with which the photon interacts with detector crystals.

(22) The non-transitory computer-readable storage medium according to any of (17) to (21), wherein the method further comprises displaying an image based on the data associated with each group of the grouped pairs of photons after applying the corresponding interaction-property-specific correction kernel.

(23) The non-transitory computer-readable storage medium according to any of (17) to (22) wherein the corresponding interaction-property-specific correction kernel uses ordered subset expectation maximization on subsets of the entire data set for each image update.

(24) The non-transitory computer-readable storage medium according to any of (17) to (23), wherein the instruction that cause the computer to perform selecting, for each group of the grouped pairs of photons, a corresponding interaction-property-specific correction kernel, and applying the corresponding interaction-property-specific correction kernel to data associated with each group of the grouped pairs of photons includes, but is not limited to, instruction that cause the computer to perform selecting, for each group of the grouped pairs of photons, a corresponding interaction-property-specific point spread function correction kernel, and applying the corresponding interaction-property-specific point spread function correction kernel to data associated with each group of the grouped pairs of photons.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A medical imaging scanner, comprising:
processing circuitry configured to:
receive list-mode data generated by detecting radiation emitted from a radiation source positioned with a field of view of the medical imaging scanner, each event of a plurality of events within the list-mode data including two photons,
classify each photon included in the list-mode data based on at least one interaction property of the photon,
generate grouped pairs of photons based on the classification of each photon included in the list-mode data based on the at least one interaction property of the photon,
select, for each group of the grouped pairs of photons, a corresponding interaction-property-specific correction kernel, and
apply the corresponding interaction-property-specific correction kernel to data associated with each group of the grouped pairs of photons.

2. The medical imaging scanner of claim 1, wherein the data associated with each group of the grouped pairs of photons is image data.

3. The medical imaging scanner of claim 1, wherein the data associated with each group of the grouped pairs of photons is sinogram data.

4. The medical imaging scanner of claim 1, wherein the at least one interaction property includes a number of detector crystals a photon interacts with.

5. The medical imaging scanner of claim 1, wherein the at least one interaction property includes an energy with which each photon interacts with detector crystals.

6. The medical imaging scanner of claim 1, wherein the processing circuitry is further configured to display an image based on the data associated with each group of the grouped pairs of photons after applying the corresponding interaction-property-specific correction kernel.

7. The medical imaging scanner of claim 1, wherein the processing circuitry is further configured to display an image based on the data associated with each group of the group pairs of photons wherein ordered subset expectation maximization uses interaction-property-specific correction kernel on subsets of the entire data set for each image update.

8. The medical imaging scanner of claim 1, wherein the processing circuitry configured to select, for each group of the grouped pairs of photons, a corresponding interaction-property-specific correction kernel, and apply the corresponding interaction-property-specific correction kernel to data associated with each group of the grouped pairs of photons comprises processing circuitry configured to select, for each group of the grouped pairs of photons, a corresponding interaction-property-specific point spread function correction kernel, and apply the corresponding interaction-property-specific point spread function correction kernel to data associated with each group of the grouped pairs of photons.

9. An image construction method comprising:
receiving list-mode data generated by detecting radiation emitted from a radiation source positioned with a field of view of an medical imaging scanner, each event of a plurality of events within the list-mode data including two photons;
classifying each photon included in the list-mode data based on at least one interaction property of the photon;
generating grouped pairs of photons based on a result of the classifying of each photon included in the list-mode data based on at least one interaction property of the photon;
selecting, for each group of the grouped pairs of photons, a corresponding interaction-property-specific correction kernel; and
applying the corresponding interaction-property-specific correction kernel to data associated with each group of the grouped pairs of photons.

10. The method of claim 9, wherein the data associated with each group of the grouped pairs of photons is image data.

11. The method of claim 9, wherein the data associated with each group of the grouped pairs of photons is sinogram data.

12. The method of claim 9, wherein the at least one interaction property includes a number of detector crystals a photon interacts with.

13. The method of claim 9, wherein the at least one interaction property includes an energy with which the photon interacts with detector crystals.

14. The method of claim 9, further comprising displaying an image based on the data associated with each group of the grouped pairs of photons after applying the corresponding interaction-property-specific correction kernel.

15. The method of claim 9, wherein the corresponding interaction-property-specific correction kernel uses ordered subset expectation maximization on subsets of the entire data set for each image update.

16. The method of claim 9, wherein selecting, for each group of the grouped pairs of photons, a corresponding interaction-property-specific correction kernel, and applying the corresponding interaction-property-specific correction kernel to data associated with each group of the grouped pairs of photons comprises selecting, for each group of the grouped pairs of photons, a corresponding interaction-property-specific point spread function correction kernel, and applying the corresponding interaction-property-specific point spread function correction kernel to data associated with each group of the grouped pairs of photons.

17. A non-transitory computer-readable storage medium storing computer-readable instructions that, when executed by a computer, cause the computer to perform a method for reconstructing a positron emission tomography image, comprising
receiving list-mode data generated by detecting radiation emitted from a radiation source positioned with a field of view of an medical imaging scanner, each event of a plurality of events within the list-mode data including two photons;
classifying each photon included in the list-mode data based on at least one interaction property of the photon;
generating grouped pairs of photons based on a result of the classifying of each photon included in the list-mode data based on at least one interaction property of the photon;
selecting, for each group of the grouped pairs of photons, a corresponding interaction-property-specific correction kernel; and applying the corresponding interaction-property-specific correction kernel to data associated with each group of the grouped pairs of photons.

18. The non-transitory computer-readable storage medium according to claim 17, wherein the at least one interaction property includes a number of detector crystals a photon interacts with.

19. The non-transitory computer-readable storage medium according to claim 17, wherein the at least one interaction property includes an energy with which the photon interacts with detector crystals.

20. The non-transitory computer-readable storage medium according to claim 17, wherein the method further comprises displaying an image based on the data associated with each group of the grouped pairs of photons after applying the corresponding interaction-property-specific correction kernel.

* * * * *